(12) United States Patent
Hussam

(10) Patent No.: US 10,339,500 B2
(45) Date of Patent: Jul. 2, 2019

(54) PATIENT EDUCATION MODULES

(71) Applicant: Ali Adel Hussam, Columbia, MO (US)

(72) Inventor: Ali Adel Hussam, Columbia, MO (US)

(73) Assignee: Universal Research Solutions, LLC, Columbia, MO (US)

(*) Notice: Subject to any disclaimer, the term of this patent is extended or adjusted under 35 U.S.C. 154(b) by 0 days.

(21) Appl. No.: 13/648,653

(22) Filed: Oct. 10, 2012

(65) Prior Publication Data

US 2014/0099616 A1    Apr. 10, 2014

Related U.S. Application Data

(60) Provisional application No. 61/583,069, filed on Jan. 4, 2012.

(51) Int. Cl.
| | | |
|---|---|---|
| G09B 5/02 | (2006.01) | |
| G09B 19/00 | (2006.01) | |
| G06Q 10/10 | (2012.01) | |
| G06Q 50/24 | (2012.01) | |
| G09B 23/28 | (2006.01) | |

(52) U.S. Cl.
CPC ........... *G06Q 10/103* (2013.01); *G06Q 50/24* (2013.01); *G09B 5/02* (2013.01); *G09B 19/00* (2013.01); *G09B 23/28* (2013.01)

(58) Field of Classification Search
CPC ...... G09B 23/28; G09B 21/006; G06Q 50/22; G06Q 50/24
USPC .......................... 434/262, 322, 323; 600/300
See application file for complete search history.

(56) References Cited

U.S. PATENT DOCUMENTS

| | | | |
|---|---|---|---|
| 6,738,754 B1 * | 5/2004 | Norman, Jr. | |
| 6,974,328 B2 * | 12/2005 | Aspe et al. | ................... 434/262 |
| 7,260,480 B1 * | 8/2007 | Brown et al. | ................... 702/19 |
| 7,668,718 B2 * | 2/2010 | Kahn et al. | ................... 704/270 |
| 7,802,183 B1 | 9/2010 | Essin | |

(Continued)

FOREIGN PATENT DOCUMENTS

| | | |
|---|---|---|
| JP | 2004-145507 | 5/2004 |
| JP | 2004-283316 | 10/2004 |

OTHER PUBLICATIONS

International Search Report & Written Opinion of Application No. PCT/US2013/020284, dated Jun. 21, 2013, pp. 1-17.

*Primary Examiner* — Samchuan C Yao
*Assistant Examiner* — Michael C Humphrey
(74) *Attorney, Agent, or Firm* — Fish & Richardson P.C.

(57) ABSTRACT

A computer-implemented method comprising: retrieving, by one or more computer systems, a patient education module for educating a patient about a medical procedure; wherein a structure of the patient education module comprises a first educational section and a second educational section; where the first educational section comprises information and one or more visualizations related to a first stage of the medical procedure; wherein the second educational section comprises information and one or more visualizations related to a second stage of the medical procedure; transmitting, to a device used by the patient, the patient education module for the patient to review the patient education module; receiving, from the device used by the patient, information specifying that the patient has reviewed and understood one or more of the first educational section and the second educational section.

21 Claims, 10 Drawing Sheets

(56) References Cited

U.S. PATENT DOCUMENTS

| | | | |
|---|---|---|---|
| 7,970,628 B2* | 6/2011 | Kuo et al. | 705/2 |
| 2005/0233290 A1* | 10/2005 | Jackson | 434/262 |
| 2007/0198296 A1* | 8/2007 | Pellinat | G06F 19/322 |
| | | | 705/2 |
| 2007/0299694 A1* | 12/2007 | Merck | 705/3 |
| 2008/0003555 A1* | 1/2008 | Ekvall et al. | 434/262 |
| 2008/0300915 A1 | 12/2008 | Molmenti et al. | |
| 2009/0130641 A1* | 5/2009 | Mahesh et al. | 434/262 |
| 2009/0287068 A1 | 11/2009 | Li et al. | |
| 2009/0313043 A1 | 12/2009 | Schoenberg | |
| 2010/0081118 A1 | 4/2010 | Dixit | |
| 2011/0161107 A1* | 6/2011 | Goldberg et al. | 705/3 |
| 2011/0172499 A1* | 7/2011 | Simons-Nikolova et al. | |
| | | | 600/300 |
| 2011/0191122 A1 | 8/2011 | Kharraz Tavakol et al. | |
| 2012/0310670 A1* | 12/2012 | Pruitt | 705/3 |
| 2013/0004930 A1* | 1/2013 | Sorenson et al. | 434/350 |
| 2013/0236871 A1* | 9/2013 | Weidner, Jr. | 434/262 |
| 2013/0266920 A1* | 10/2013 | Ito et al. | 434/319 |
| 2013/0309640 A1* | 11/2013 | Sanders et al. | 434/178 |
| 2013/0339052 A1* | 12/2013 | Neff | 705/3 |

\* cited by examiner

PATIENT EDUCATION MODULES

CLAIM OF PRIORITY

This application claims priority under 35 U.S.C. § 119(e) to provisional U.S. Patent Application No. 61/583,069, filed on Jan. 4, 2012, the entire contents of which are hereby incorporated by reference.

BACKGROUND

An electronic medical record ("EMR") is a computerized medical record created in an organization that delivers care, such as a hospital and/or a doctor's office. EMRs may be a part of a local stand-alone health data system that allows storage, retrieval and modification of records.

SUMMARY

In general, one innovative aspect of the subject matter described in this specification can be embodied in methods that include the actions of retrieving, by one or more computer systems, a patient education module for educating a patient about a medical procedure; wherein a structure of the patient education module includes a first educational section and a second educational section; where the first educational section includes information and one or more visualizations related to a first stage of the medical procedure; wherein the second educational section includes information and one or more visualizations related to a second stage of the medical procedure; transmitting, to a device used by the patient, the patient education module for the patient to review the patient education module; receiving, from the device used by the patient, information specifying that the patient has reviewed and understood one or more of the first educational section and the second educational section.

Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In particular, one embodiment may include all the following features in combination. In some examples, the features include structuring the patient education module into a first educational section and a second educational section; generating, for the first educational section, the information and the one or more visualizations related to the first stage of the medical procedure; assigning, to the first educational section, the generated information and the one or more visualizations related to the first stage of the medical procedure; generating, for the second educational section, the information and the one or more visualizations related to the second stage of the medical procedure; and assigning, to the second educational section, the generated information and the one or more visualizations related to the second stage of the medical procedure.

In other implementations, the features include retrieving an electronic medical record that is associated with the patient; identifying one or more medical codes in the electronic medical record; searching, in a database, for patient education modules with medical codes corresponding to the medical code included in the electronic medical record; and identifying, based on a searching, a patient education module with a medical code corresponding to the medical code included in the electronic medical record; wherein retrieving the patient education module includes: retrieving the identified patient education module.

In still other implementations, patient education modules are associated with unique identifiers, and the method further includes: receiving, from a device used by a medical service provider, a message including content for a patient education module, wherein the message includes a unique identifier for the content; searching, in a database storing the patient education modules, for a patient education module with a unique identifier corresponding to the unique identifier for the content; identifying, based on searching, a patient education module with a unique identifier corresponding to the unique identifier for the content; and assigning the content to the identified patient education module.

In still other implementations, the method includes receiving a request for a patient education module that is related to a medical procedure to be performed on a patient; and selecting, from a set of patient education modules, the patient education module that is related to the medical procedure, wherein selecting is based on a type of the medical procedure. In yet other implementations, the first educational section includes a graphical user interface for the patient to confirm review of the first educational section and to indicate consent to the procedure addressed by the first educational section, the method further includes: tracking an amount of time the patient spends reviewing the first educational section; receiving, from the device used by the user through the graphical user interface, information confirming the review and indicating the consent; comparing the tracked amount of time to a threshold amount of time; determining, based on comparing, that the tracked amount of time is less than the threshold amount of time; and in response to determining that the tracked amount of time is less than the threshold amount of time, performing one or more operations including: sending, to the device used by the patient, a message notifying the patient to re-review the first educational section; and sending, to a device associated with a medical service provider, a notification that that patient may have inadequately reviewed the first educational section.

In yet other implementations, the patient education module includes a first patient education module, wherein the medical procedure includes a first medical procedure, and the method further includes: retrieving, by the one or more computer systems, a second patient education module for educating the patient about a second medical procedure; wherein the first patient education module differs from the second patient education module; wherein the first medical procedure differs from the second medical procedure. In still other implementations, the features include structuring the first educational section to include a series of trays, wherein a tray includes a collection of information associated with a category specified by the tray.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE FIGURES

Like reference symbols in the various drawings indicate like elements.

DETAILED DESCRIPTION

Described herein is a system for providing a patient with various patient education modules. Generally, a patient education module includes a collection of information to promote an education of a patient regarding an area of medicine and/or a medical service, including, e.g., a particular medical topic, a particular medical procedure, a particular medical surgery, and so forth. Types of information included in a patient education module include consent forms, pamphlets describing the process of a medical procedure and possible outcomes, visualizations of areas of the anatomy where a medical procedure is being performed, information describing potential risks and side effects of a procedure, pre-operative information, information describing how to prepare for a surgery, post-operative information, information describing medical conditions, visualizations of a patient's anatomy in a normal condition, pre-operative condition, in a post-operative condition, and so forth.

Figure 1A:
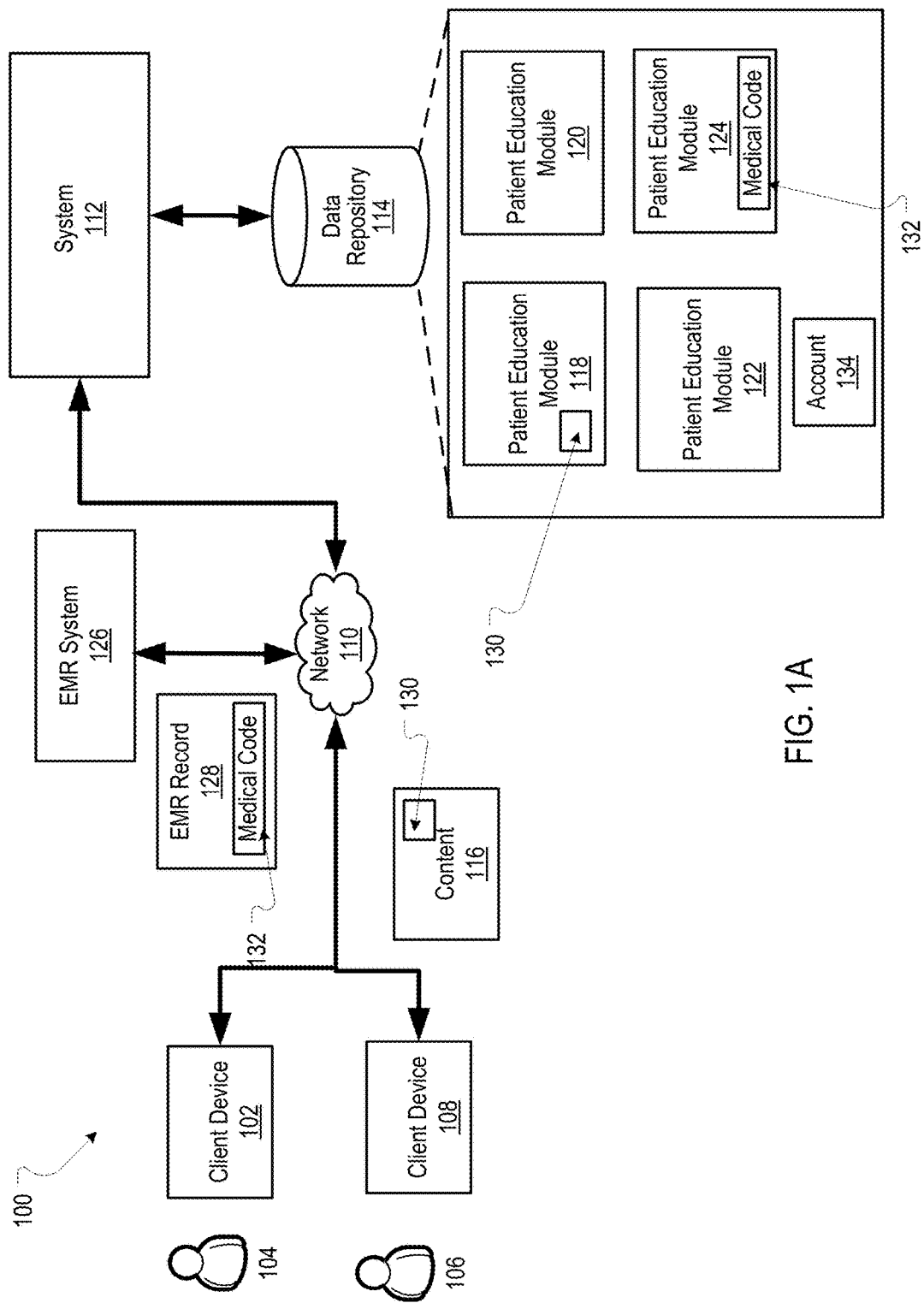
FIG. 1A is a conceptual diagram of a network environment for generating patient education modules.

FIG. 1A is a conceptual diagram of network environment 100 for generating patient education modules 118, 120, 122, 124. System 100 includes network 110, client devices 102, 104, EMR system 126, system 112, and data repository 114. In the example of FIG. 1A, system 112 is configured to generate patient education modules, including, e.g., patient education modules 118, 120, 122, 124.

In an example, client device 102 is used by user 104. In this example, user 104 is a medical service provider. In this example, user 104 may want to generate a patient education module that user 104 can provide to patients to educate the patients about an upcoming medical procedure and to receive consent to perform the medical procedure. In this example, the medical procedure is a knee replacement surgery. In this example, user 104 uses client device 102 to transmit, to system 112, content 116 for a patient education module. In this example, content 116 is created by user 104 (and/or by an administrator associated with user 104) and is specific to a practice associated with user 104.

In this example, user 104 may send, to system 112, a request to generate a patient education module that includes content that is provided by user 104. In response to the request, system 112 generates a patient education module, including, e.g., patient education module 118. System 112 includes unique identifier 130 in patient education module 118. In this example, system 112 sends, to client device 102, information notifying user 102 that patient education module 118 has been generated and information specifying unique identifier 126. In this example, when client device 102 sends content 116 to system 112, client device 102 embeds unique identifier 130 in content 116.

Upon receipt of content 116, system 112 searches data repository 114 for patient education modules with a unique identifier that matches unique identifier 130 included in content 116. In this example, system 112 identifies that patient education module 118 is associated with unique identifier 130 that matches unique identifier 130 included in content 116. Based on the match, system 112 identifies that content 116 is for patient education module 118. Accordingly, system 112 adds content 116 to patient education module 118.

In another example, client device 108 is used by user 106. In this example, user 106 includes a patient, including, e.g., a patient that is being seen by user 104. System 112 is configured to identify which ones of patient education modules 118, 120, 122, 124 are pertinent to user 106. There are various ways in which system 112 may determines which ones of patient education modules 118, 120, 122, 124 are pertinent to user 106. In some examples, user 106 is provided an account to gain access to system 112. In this example, system 112 tracks upcoming appointments and/or procedures for user 106. System 112 may track the upcoming appointments, e.g., by retrieving data from an external appointment booking system. When system 112 identifies an appointment of user 106, system 112 may send a message to a medical service provider associated with the appointment for instructions as to which patient education modules to associate with user 106.

In another example, system 112 may use EMR record 128 for user 106 in identifying which ones of patient education modules 118, 120, 122, 124 to assign to user 106 (and/or an account of user 106 in system 112). In this example, EMR system 126 is configured to store EMR records for various users. Generally, an EMR record includes an electronic version of a patient's medical record. In this example, EMR record 128 includes various medical codes, including, e.g., medical code 132. Generally, a medical code includes information uniquely identifying a particular type of diagnosis, medical condition, medical procedure, and so forth. There are various types of medical codes, including, e.g., diagnosis codes, International Statistical Classification of Diseases and Related Health Problems ("ICD") codes (e.g., ICD-9 and ICD-10 codes), Current Procedural Terminology ("CPT") codes and other various diagnosis information and treatment information.

In the example of FIG. 1A, one or more of patient education modules 118, 120, 122, 124 are associated with medical codes. For example, patient education module 124 is associated with medical code 132. There are various ways in which system 112 identifies medical codes to be associated with patient education modules. In some examples, content 116 includes information specifying medical codes to be associated with the patient education module specified by unique identifier 130. In another example, system 112 may identify medical codes to be associated with patient education modules based on the contents of patient education modules. In this example, the medical codes may be associated with descriptions or other information specifying types of information that are classified or otherwise associated with the medical codes. Using the descriptions of the medical codes and the contents of the patient education modules, system 112 identifies medical codes with descriptions that are related to the contents of the patient education modules, e.g., based on word matching and/or similarity between words in the descriptions of the medical codes and the contents of the patient education modules.

In the example of FIG. 1A, system 112 uses the medical codes included in EMR record 128 and the medical codes associated with one or more of patient education modules 118, 120, 122, 124 to identify which patient education modules are assigned to user 106, e.g., based on matches and/or similarities among medical codes in EMR record 128 and medical codes associated with patient education modules 118, 120, 122, 124. In this example, user 106 is associated with account 134 on system 112. In this example, account 134 is specific to user 106. When system 112 identifies a correspondence between medical code 132 in EMR record 128 and medical code 132 that is associated with patient education module 124, system 112 assigns the patient education module 124 to account 134. Generally, a correspondence includes a similarity and/or a match among items of data.

Figure 1B:
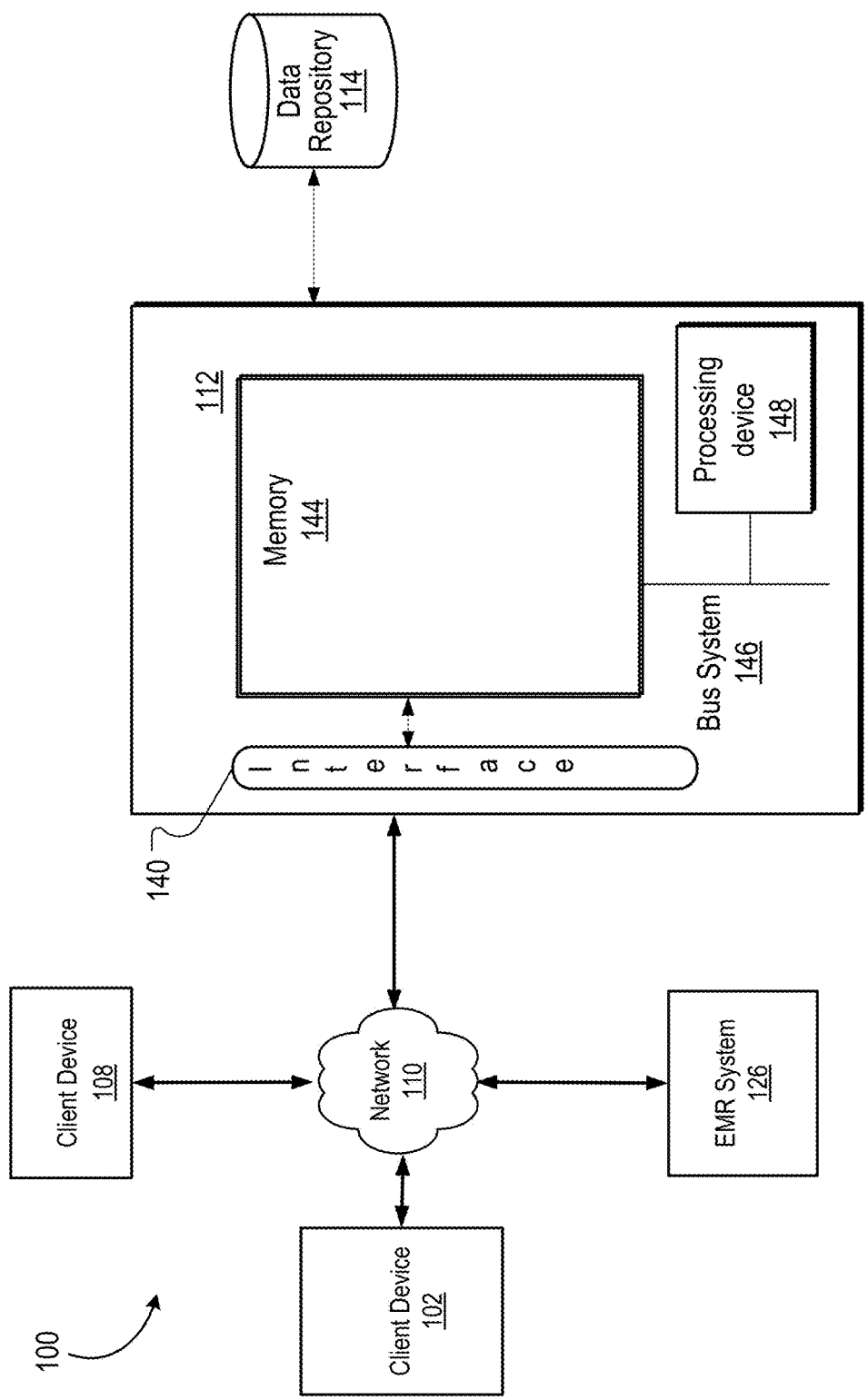
FIG. 1B is a block diagram of components of the network environment for generating patient education modules.

FIG. 1B is a block diagram of components of the network environment for generating patient education modules. In FIG. 1B, client devices 104, 106 can be any sort of computing devices capable of taking input from a user and communicating over network 110 with system 112 and/or with other client devices. For example, client devices 104, 106 can be mobile devices, desktop computers, laptops, cell phones, personal digital assistants ("PDAs"), servers, embedded computing systems, and so forth.

System 112 can be any of a variety of computing devices capable of receiving data, such as a server, a distributed computing system, a desktop computer, a laptop, a cell phone, a rack-mounted server, and so forth. System 112 may be a single server or a group of servers that are at a same location or at different locations.

The illustrated system 112 can receive data from client devices 104, 106 and from EMR system 126 via input/output ("I/O") interface 140. I/O interface 140 can be any type of interface capable of receiving data over a network, such as an Ethernet interface, a wireless networking interface, a fiber-optic networking interface, a modem, and so forth. System 112 also includes a processing device 148 and memory 144. A bus system 146, including, for example, a data bus and a motherboard, can be used to establish and to control data communication between the components of system 112.

The illustrated processing device 148 may include one or more microprocessors. Generally, processing device 148 may include any appropriate processor and/or logic that is capable of receiving and storing data, and of communicating over a network (not shown). Memory 144 can include a hard drive and a random access memory storage device, such as a dynamic random access memory, or other types of non-transitory machine-readable storage devices. Memory 144 stores computer programs (not shown) that are executable by processing device 148 to perform the techniques described herein.

Figure 2:
FIGS. 2-8 are examples of graphical user interfaces included in patient education modules.

Referring to FIG. 2, system 112 generates graphical user interface 200 for user 106 to log into account 134. In some example, user 106 receives an email from a medical institution (e.g., a medical institution associated with user 104) that includes a link to graphical user interface 200. In the example of FIG. 2, graphical user interface 200 includes link 202. Through selection of link 202, user 106 may access and may view content of patient education module 124.

Figure 3:
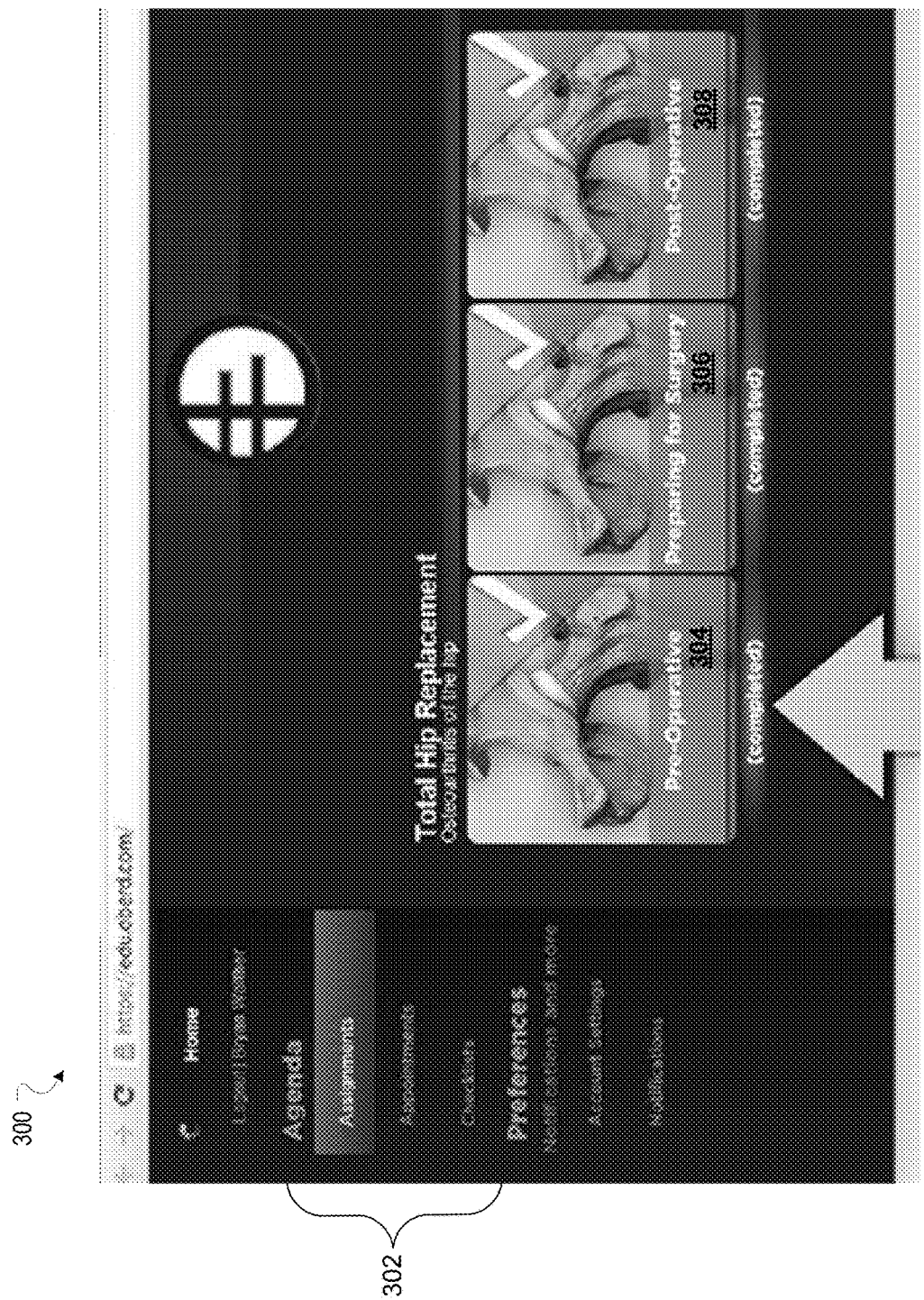

Referring to FIG. 3, graphical user interface 300 is displayed (e.g., on client device 108), e.g., following user 106 logging into account 134. In this example, graphical user interface 300 displays a dashboard view of the contents of patient education module 124. For example, graphical user interface 300 includes portion 302 for display of an agenda of user 106. In this example, portion 302 displays information specifying assignments that user 106 need to complete. Generally, an assignment includes information for a patient to review and/or questions for a patient to answer. Portion 302 also displays information specifying appointments and checklists. Generally, a checklist includes a visual indication of actions a patient needs to perform, e.g., prior to a procedure and/or appointment.

Graphical user interface 300 also includes visualizations 304, 306, 308. In this example, various portions of patient education module 124 include content that is related to various stages of a procedure, including, e.g., pre-operative content, content related to preparing for surgery and post-operative content. In this example, patient education module 124 provides user 106 with various assignments and/or checklists to be completed for each of the various stages. Visualizations 304, 306, 308 provide time-chronicled indicators of progress of user 106 in completing content that is related to various stages of a procedure. For example, visualization 304 provides a visual indication of completion of the pre-operative content. Visualization 306 provides a visual indication of completion of content related to preparing for surgery. Visualization 308 provides a visual indication of completion of the post-operative content.

In an example, one or more of visualizations 304, 306, 308 are selectable, e.g., for display of assignments related to the type of content associated with visualizations 304, 306, 308. For example, selection of visualization 304 causes client device 106 to display content of patient education module 124 that is related to pre-operative content.

Figure 4:
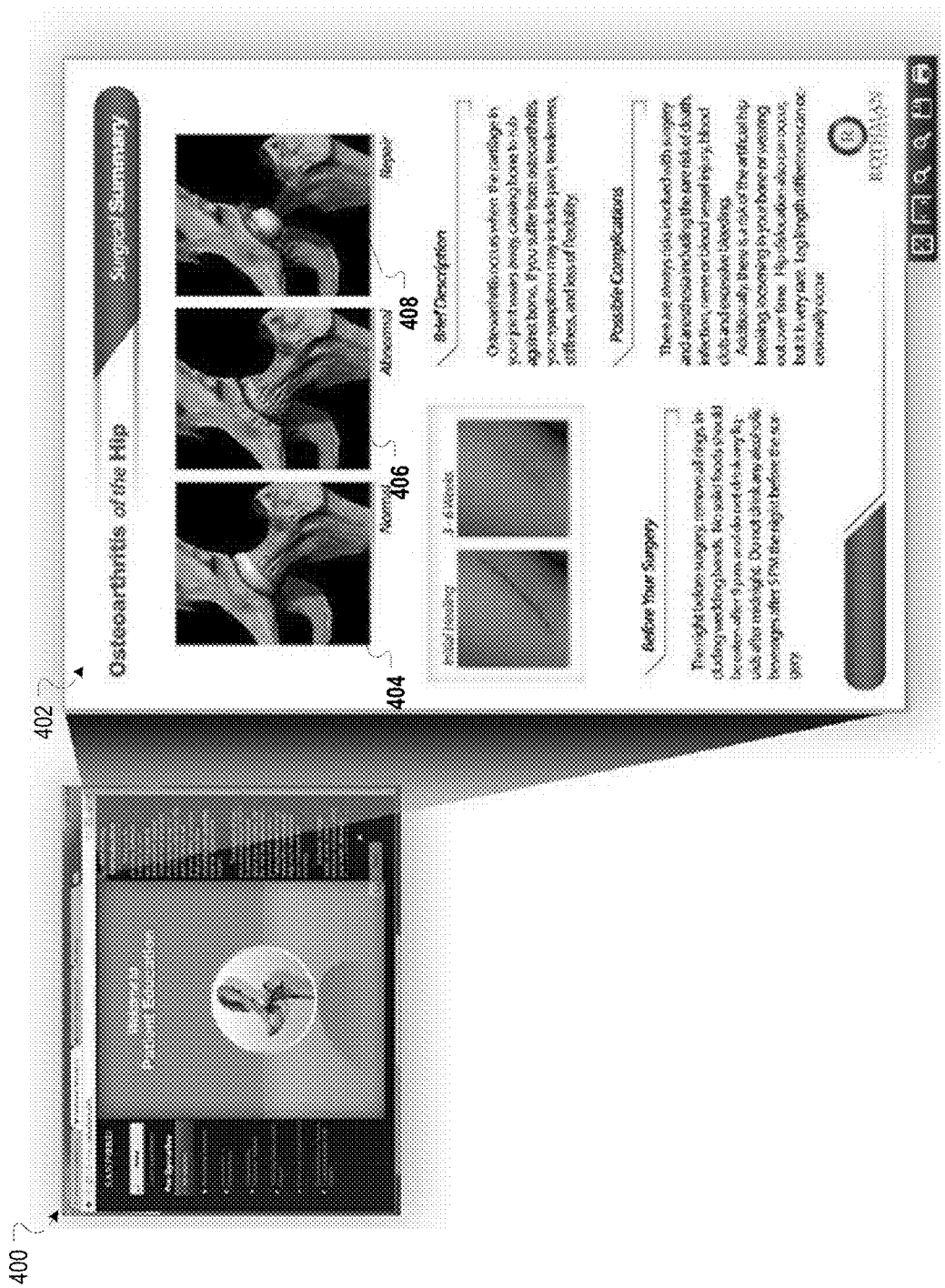

Referring to FIG. 4, graphical user interface 400 displays pre-operative content, e.g., that is included in patient education module 124. In this example, graphical user interface 400 also displays selectable portions for display of summary sheets. Generally, a summary sheet includes information specifying an overview (e.g., a summary) of content (e.g., the pre-operative content). In the example of FIG. 4, summary sheet 402 is shown. In this example, summary sheet 402 is printable and is displayed in PDF format. Summary sheet 402 includes visualizations 404, 406, 408 for display of images showing a normal portion of the anatomy on which the patient is having a procedure, an abnormal portion of the anatomy, and the anatomy following repair, respectively.

Figure 5:

Referring to FIG. 5, graphical user interface 500 displays contents of a portion of patient education module 124 that include visualizations of an area of the anatomy. In this example, visualization 504 includes an image of an area of the anatomy, including, e.g., an area of the anatomy that a patient is scheduled for surgery. Using control 502, a user may rotate visualization 504, e.g., to view different areas of the anatomy represented by visualization 504. In this example, control 502 may be used to rotate visualization 502 three-hundred sixty degrees. Visualization includes a three-dimensional visualization. While FIG. 5 illustrates a visualization of an area of the anatomy in a particular condition (e.g., the normal condition), system 112 may be configured to display a rotatable visualization of the area of the anatomy in various, other conditions (e.g., an abnormal condition, a repaired condition, and so forth).

As previously described, portions of patient education module 124 may include content for the various stages of a procedure, including, e.g., pre-operative content, content in preparation for the procedure, and post-operative content. In this example, the content in patient education module 124 is assigned to various educational sections, with an educational section including the content for a particular stage of a procedure. For example, system 112 may be configured to structure the contents of patient education module 124 into various sections. In this example, after a user has completed review of content for a particular educational section, system 112 prompts the user for verification and confirmation that the user has reviewed and accepts the content presented to the user.

Referring back to FIG. 1A, patient education modules 118, 120, 122, 124 may include information for the various stages of a medical procedure. For example, patient education module 118 may include content for the pre-operative stage. Patient education module 120 may include content for the stage of preparing for surgery. Patient education module 122 may include content for the post-operative stages. In this example and using the techniques disclosed herein, system 112 may select one or more of patient education modules 118, 120, 122, 124 to present user 106 with the educational materials associated with a particular medical procedure.

Graphical user interface 500 includes various trays 506, 508, 510, 512, 514, 516, 518. Generally, a tray may include a portion of a graphical user interface that when selected causes an update to a type of information displayed in a graphical user interface. In this example, tray 506 is for display of introductory information, including, e.g., information describing the various educational sections of the patient education module and contents of a particular educational section of the patient education module. Tray 508 is for display of information that describes a particular condition (e.g., normal condition) of an area of the anatomy (e.g., the hip). Tray 510 is for display of information that describes a particular disease of an area of the anatomy (e.g., the hip). Tray 512 is for display of information that describes treatment options. Tray 514 is for display of information that describes a procedure to be performed on the area of the anatomy. Tray 516 is for display of information that describes possible risks and complications to be reviewed by the patient to ensure the patient is aware of critical information. Tray 518 is for display of information that confirms that the patient has review the information included in the various trays for an educational section of the patient education module. In an example, one or more of the foregoing trays may be included in any of the graphical user interfaces generated by system 112.

System 112 structures an educational section of a patient education module to include a series of trays, wherein a tray includes a collection of information associated with a category specified by the tray. In this example, a tray is associated with a category indicative of a type of information. By structuring the contents of an education section into a series of trays, system 112 structures the contents by assigning the contents to various categories.

Figure 6:
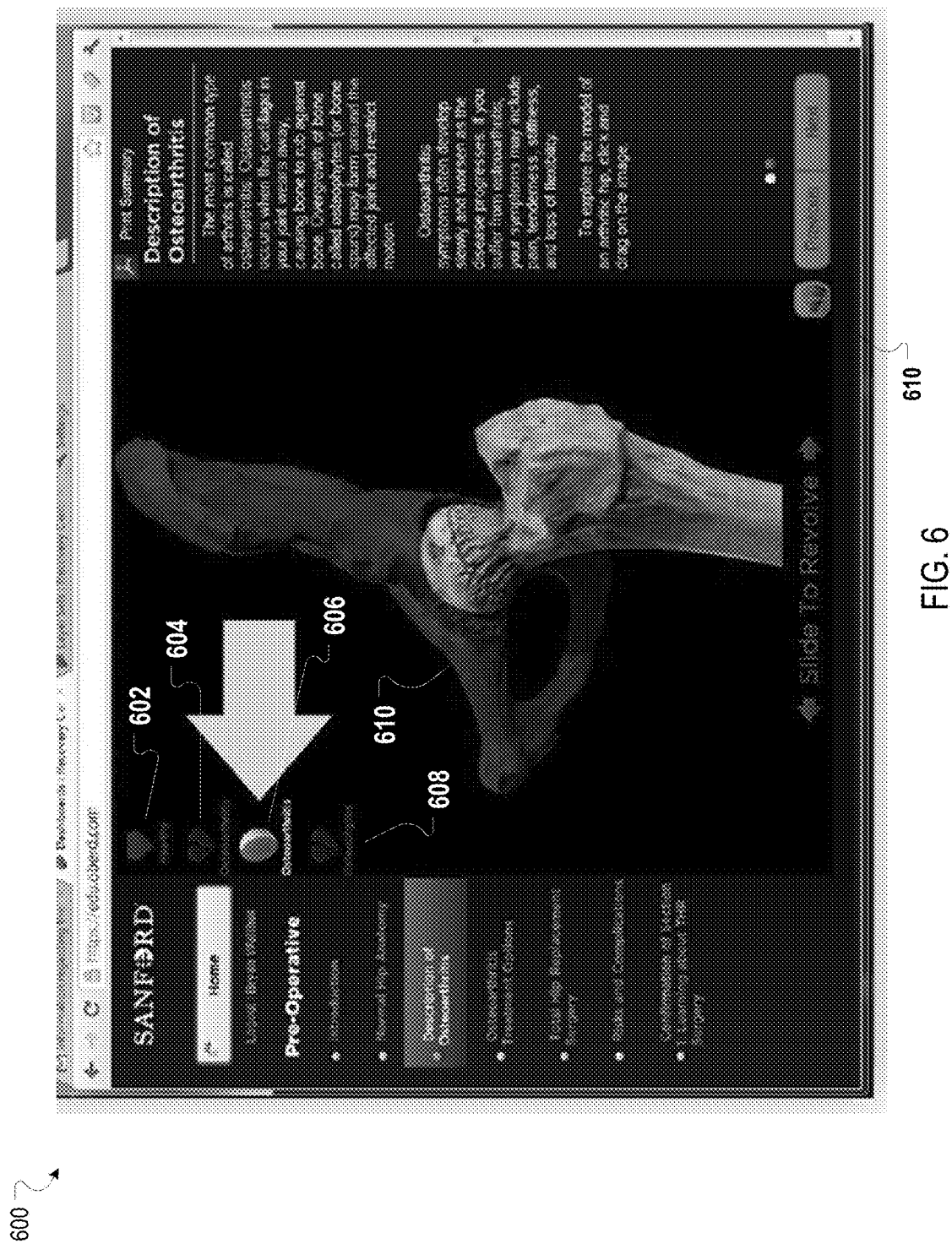

In an example, a patient can toggle through different views of a condition, e.g., using controls providing in a graphical user interface. Referring to FIG. 6, graphical user interface 600 includes controls 602, 604, 606, 608 for a patient to select to view various conditions that are associated with the patient. Graphical user interface 600 also includes visualization 610. In this example, selection of one of controls 602, 604, 606, 608 causes a portion of visualization 610 to be highlighted. In this example, the highlighted portion of visualization 610 corresponds to a portion of the anatomy that is affected by a condition selected through controls 602, 604, 606, 608. Graphical user interface 600 also includes control 610 for text to speech narration that allows the patient to both read and listen to the education material.

Figure 7:
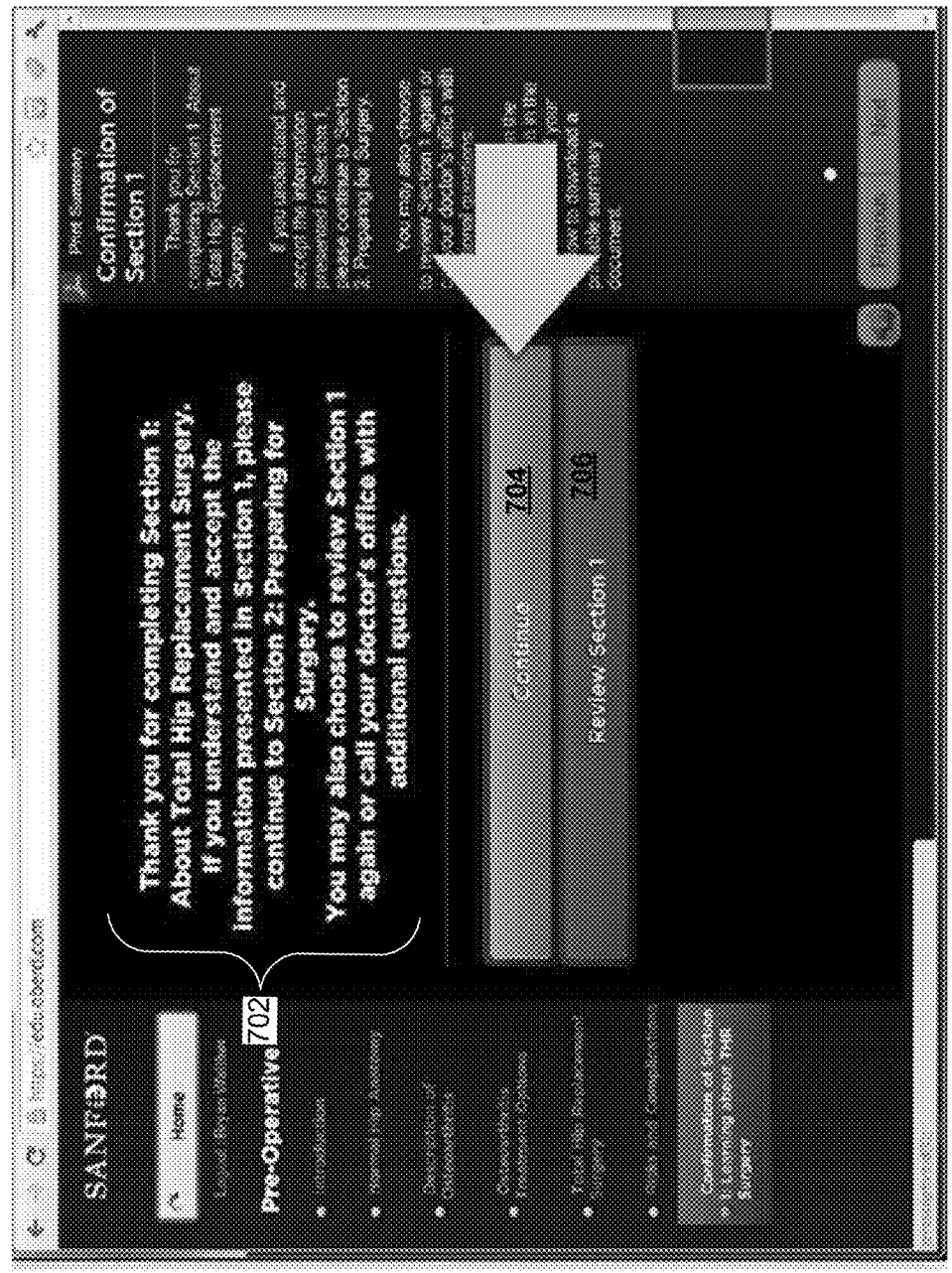

Referring to FIG. 7, graphical user interface 700 displays message 702 informing the user of completion of a particular educational section of patient education module 124. Graphical user interface 700 also includes control 704 for a patient to confirm that he has reviewed and understood the contents of the educational section. Upon selection of control 704, the patient sends to system 112 information specifying a confirmation that the patient has reviewed and understands the information. Upon selection of control 704, the patient sends to system 112 information specifying that the patient would like to review again the educational section.

In an example, system 112 is configured tracks an amount of time a user (e.g., user 106) spends on review of an educational section. In this example, system 112 stores, in data repository 114, information specifying a threshold, e.g., a threshold amount of time that the user needs to spend reviewing an educational section. In this example, when a user selects control 704, system 112 compares the tracked amount of time the user has spent reviewing the educational section to the threshold. If the tracked amount of time is less than the threshold, system 112 may perform various actions, including, e.g., requesting that the user re-review the educational section, preventing the user from sending confirmation of completion of the educational section, sending a notification to a medical service provider (e.g., a physician performing the procedure), and so forth. That is, through control 704, patients are prompted to verify their understanding of the material and to provide an electronic consent for the procedures addressed in the section. Actions throughout the module are fully tracked, including time spent, and reported to a dashboard. Compliance and consent indicators are supplemented by special alerts for times that suggest insufficient review of the material in the institution's dashboard.

Figure 8:
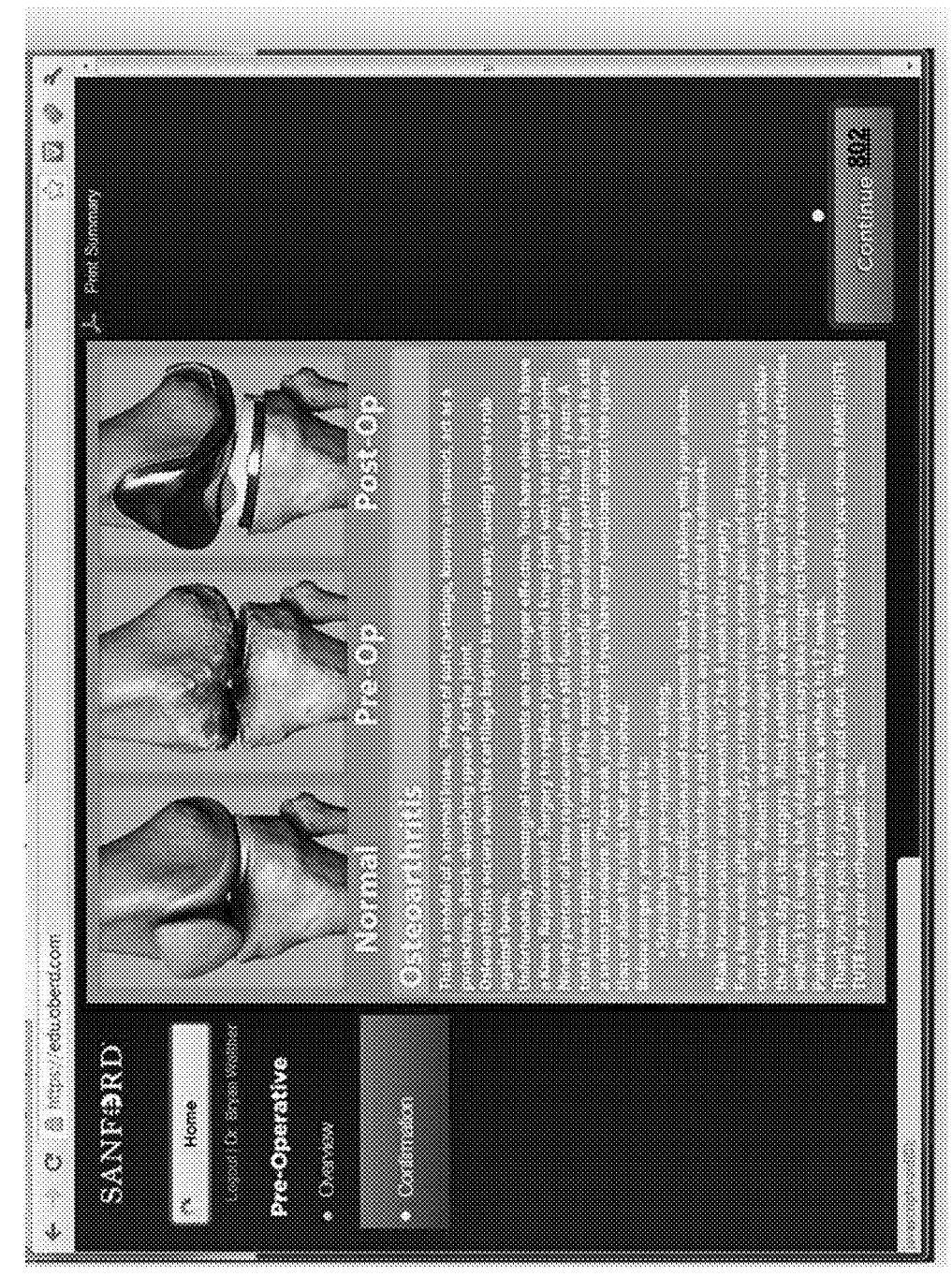

In addition to prompting the patient for consent to perform the medical procedure, system 112 may also prompt physicians to confirm assignments and review of material with patients. Referring to FIG. 8, graphical user interface 800 displays, for a physician, control 802, through which the physician can confirm assignments and review of material with patients.

Figure 9:
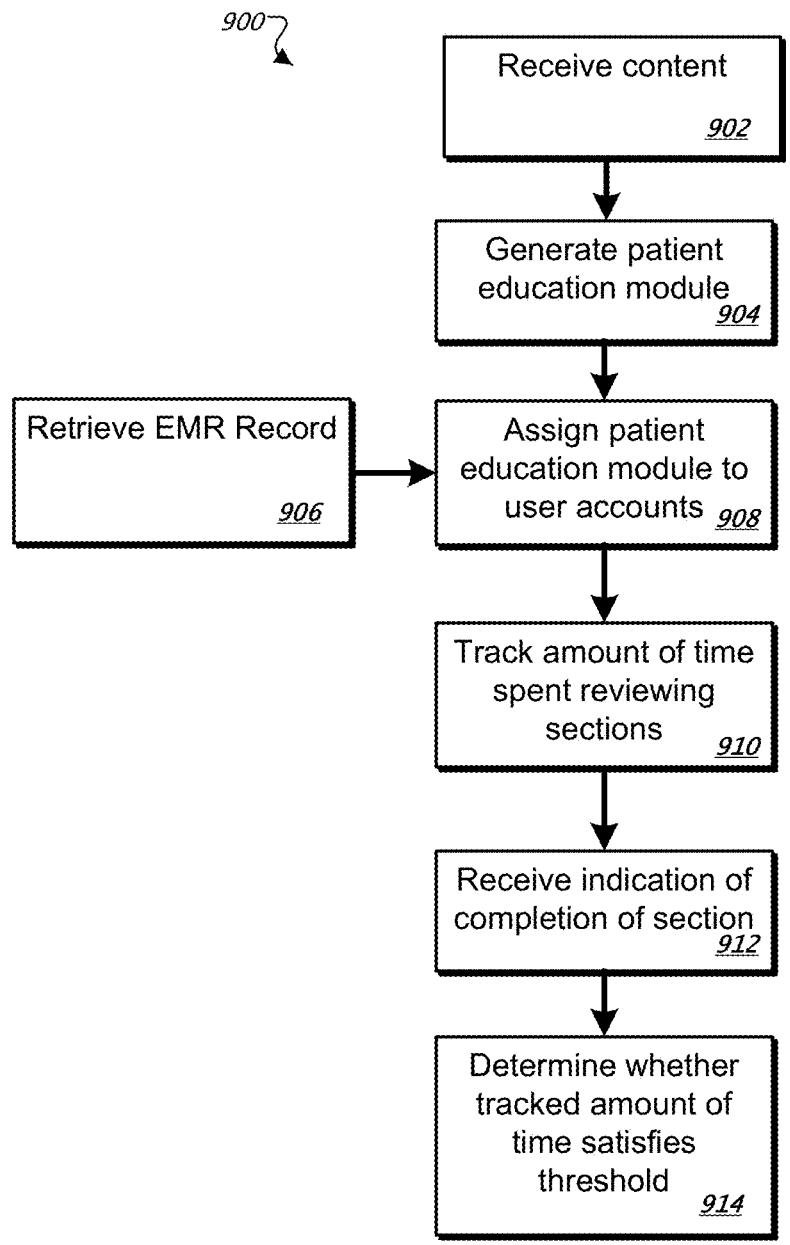
FIG. 9 is a flow chart of an example of a process for implementing a patient education module.

FIG. 9 is a flow chart of an example of process 900 for implementing a patient education module. In operation, system 112 receives (902) content, including, e.g., content 116. Using the received content, system 112 generates (904) a patient education module, including, e.g., one of patient education modules 118, 120, 122, 124. In this example, system 112 may generate the patient education module by generating a shell for the patient education module. Generally, a shell includes a data structure to be populated with data. In this example, upon receipt of the content, system 112 populates the shell with the content.

System 112 also retrieves (906), from EMR system 126, an EMR record, including, e.g., EMR record 128. Using contents of the retrieved EMR record (e.g., medical codes included in the EMR record), system 112 assigns (908) a patient education module to a user associated with the retrieved EMR record. In an example, system 112 assigns the patient education module to a user by assigning the patient education module to an account associated with the user.

In the example of FIG. 9, system 112 tracks (910) an amount of time spent reviewing the various educational sections of a patient education module. System 112 also receives (912) an indication of completion of an educational section. In this example, system 112 receives the indication from client device 108. Using the tracked amount of time and a threshold amount of time, system 112 determines (914) whether the tracked amount of time satisfies the threshold amount of time (e.g., whether the tracked amount of time exceeds the threshold amount of time). If system 112 determines that the tracked amount of time exceeds the threshold amount of time, then system 112 allows a user to indicate consent to the procedure and/or to submit confirmation that the user has reviewed the educational section. If system 112 determines that the tracked amount of time does not satisfy the threshold amount of time, then, in some examples, system 112 notifies the patient and/or prompts the patient to re-review the educational section.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be data in different formats such as text, graphics, images, sound, video, Hypertext Markup Language (HTML), as well as programs. Upon specification of a link by the user, the client computer makes a TCP/IP request to a Web server and receives data, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view data available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method of electronically obtaining consent over a network for performance of a medical procedure, the method comprising:

tracking, by one or more computer systems, one or more medical appointments by obtaining external data structured using fields of a first relational data structure that is stored in a memory device of an electronic booking system of a medical services provider and used by the external appointment booking system of the medical services provider to represent medical appointments for one or more patients, wherein the external appointment booking system is configured for communication with the one or more computer systems using the Internet that are (i) remote from the memory device of the electronic booking system of the medical services provider and (ii) configured to perform the tracking and automatic assignment of medical procedure modules to patients;

based on the tracking, automatically detecting, by the one or more computer systems, particular data obtained from the structured fields of the relational data structure that is stored in the memory device of the electronic booking system, wherein the particular data (i) represents an upcoming medical appointment for a patient and (ii) includes a key value that is used to identify the patient;

responsive to the detecting, (i) accessing, by the one or more computer systems, a second relational data structure that includes fields that structure data representing an electronic medical record (EMR) associated with the patient using the key value and (ii) analyzing, by the one or more computer systems, the EMR associated with the patient to identify, based on the data structured in the fields of the second relational data structure representing the EMR, one or more items of medical data in the EMR;

generating, by the one or more computer systems, a search query that includes search parameters based on the one or more items of medical data that were identified based on the data structured in the fields of the second relational data structure representing the EMR;

automatically executing, by the one or more computer systems, the generated search query against a database storing a plurality of potential medical procedure modules to identify a medical procedure module associated with one or more criteria that are satisfied by the parameters of the generated search query that include the one or more items of medical data that were identified based on the data structured in the fields of the second relational data structure representing the EMR, wherein the medical procedure module includes sections representing stages of a medical procedure, and wherein the sections include a first stage section and a second stage section, wherein the first and second stages each include sections for obtaining consent for a medical procedure that is represented by the identified medical procedure module;

identifying, based on the automatic execution of the generated search query by the one or more computer systems, a particular medical procedure module that is associated with the one or more criteria that are satisfied by the parameters of the search query that include the one or more items of medical data that were identified based on the data structured in the fields of the second relational data structure representing the EMR;

automatically assigning, by the one or more computer systems, the identified medical procedure module to the patient;

updating, in a first data storage device, data in a field of a third relational data structure to include first information that specifies whether one or more conditions have been satisfied to initiate an update to a webpage that can be provided by the one or more computer systems to display the second stage section;

responsive to determining, by the one or more computer systems and based on the updated data, that the one or more conditions have been satisfied to initiate an update to the webpage, transmitting, to a device used by the patient over the network, a notification to provide electronic consent, the notification including a link, wherein selection of the link causes rendering, by an application of the device, of a webpage in a display of the device that displays the first stage section of the medical procedure module;

tracking, by the one or more computer systems, a first amount of time the patient reviews the first stage section;

receiving, by the one or more computer systems and from the device used by the patient over the Internet, a fourth relational data structure that includes structured fields that represent second information indicating that the patient has input information that affirms that the patient has reviewed and understood the first stage section;

determining, by the one or more computer systems, whether the first amount of time the patient reviews the first stage section exceeds a predetermined threshold amount of time;

accessing, by the one or more computer systems, program code that correlates the first information, the second information, and data indicating that (i) the determining indicates that the first amount of time exceeds a predetermined threshold or (ii) the determining indicates that the first amount of time does not exceed a predetermined threshold;

when the correlated information includes information specifying that the first amount of time exceeds the predetermined threshold, accessing, by the one or more computer systems, computer code that enhances the first information for use in updating the webpage provided by the one or more computer systems to display the second stage section;

when the correlated information includes information specifying that the first amount of time does not exceed the predetermined threshold:

restricting, by the one or more computer systems, transmittal of the second stage section to the device used by the patient until the information specifying that the patient has input information that affirms that the patient has reviewed and understood the first stage section is received; and upon receiving the information specifying that the patient has reviewed and understood the first stage section, accessing, by the one or more computer systems, computer code that enhances the first information to initiate an update to the webpage provided by the one or more computer systems to display the second stage section; and electronically obtaining, at least partly based on first information specifying completion of the first stage section and second information specifying completion of the second stage section displayed in the webpage, consent to the medical procedure.

2. The computer-implemented method of claim 1, further comprising:
generating, for the first stage section, information and one or more visualizations related to a first stage of the medical procedure;
assigning, to the first stage section, the generated information and the one or more visualizations related to the first stage of the medical procedure;
generating, for the second stage section, information and one or more visualizations related to a second stage of the medical procedure; and
assigning, to the second stage section, the generated information and the one or more visualizations related to the second stage of the medical procedure.

3. The computer-implemented method of claim 1, wherein the first stage section comprises information and one or more visualizations related to a first stage of the medical procedure; and
wherein the second stage section comprises information and one or more visualizations related to a second stage of the medical procedure.

4. The computer-implemented method of claim 1, wherein medical procedure modules are associated with unique identifiers, and wherein the method further comprises:
receiving, from a device used by a medical service provider, a message comprising content for a medical procedure module, wherein the message comprises a unique identifier for the content;
searching, in a database storing the medical procedure modules, for a medical procedure module with a unique identifier corresponding to the unique identifier for the content;
identifying, based on searching, a medical procedure module with a unique identifier corresponding to the unique identifier for the content; and
assigning the content to the identified medical procedure module.

5. The computer-implemented method of claim 1, further comprising:
receiving a request for a medical procedure module that is related to a medical procedure to be performed on a patient; and
selecting, from a set of medical procedure modules, the medical procedure module that is related to the medical procedure to be performed, wherein selecting is based on a type of the medical procedure.

6. The computer-implemented method of claim 1, further comprising:
following a determination that the amount of time the patient reviews the first stage section does not exceed the predetermined threshold amount of time, performing one or more of operations comprising:
sending, to the device used by the patient, a message notifying the patient to re-review the first stage section; and
sending, to a device associated with a medical service provider, a notification that that patient may have inadequately reviewed the first stage section.

7. The computer-implemented method of claim 1, wherein the medical procedure module comprises a first medical procedure module, wherein the medical procedure comprises a first medical procedure, and wherein the method further comprises:
retrieving, by the one or more computer systems, a second medical procedure module for educating the patient about a second medical procedure;
wherein the first medical procedure module differs from the second medical procedure module;
wherein the first medical procedure differs from the second medical procedure.

8. The computer-implemented method of claim 1, further comprising:
structuring the first stage section to include a series of trays, wherein a tray includes a collection of information associated with a category specified by the tray.

9. One or more machine-readable hardware storage devices storing instructions that are executable by one or more processing devices to perform operations of electronically obtaining consent over a network for performance of a medical procedure, the operations comprising:
tracking one or more medical appointments by retrieving external data from an external appointment booking system that is configured for communication with one or more computer systems performing the tracking and automatic assignment of medical procedure modules to patients;
tracking, by one or more computer systems, one or more medical appointments by obtaining external data structured using fields of a first relational data structure that is stored in a memory device of an electronic booking system of a medical services provider and used by the external appointment booking system of the medical services provider to represent medical appointments for one or more patients, wherein the external appointment booking system is configured for communication with the one or more computer systems using the Internet that are (i) remote from the memory device of the electronic booking system of the medical services provider and (ii) configured to perform the tracking and automatic assignment of medical procedure modules to patients;
based on the tracking, automatically detecting, by the one or more computer systems, particular data obtained from the structured fields of the relational data structure that is stored in the memory device of the electronic booking system, wherein the particular data (i) represents an upcoming medical appointment for a patient and (ii) includes a key value that is used to identify the patient;
responsive to the detecting, (i) accessing, by the one or more computer systems, a second relational data structure that includes fields that structure data representing an electronic medical record (EMR) associated with the patient using the key value and (ii) analyzing, by the one or more computer systems, the EMR associated with the patient to identify, based on the data structured in the fields of the second relational data structure representing the EMR, one or more items of medical data in the EMR;
generating, by the one or more computer systems, a search query that includes search parameters based on the one or more items of medical data that were identified based on the data structured in the fields of the second relational data structure representing the EMR;
automatically executing, by the one or more computer systems, the generated search query against a database storing a plurality of potential medical procedure modules to identify a medical procedure module associated with one or more criteria that are satisfied by the parameters of the generated search query that include the one or more items of medical data that were identified based on the data structured in the fields of the second relational data structure representing the EMR, wherein the medical procedure module includes sections representing stages of a medical procedure, and wherein the sections include a first stage section and a second stage section, wherein the first and second stages each include sections for obtaining consent for a medical procedure that is represented by the identified medical procedure module;

identifying, based on the automatic execution of the generated search query by the one or more computer systems, a particular medical procedure module that is associated with the one or more criteria that are satisfied by the parameters of the search query that include the one or more items of medical data that were identified based on the data structured in the fields of the second relational data structure representing the EMR;

automatically assigning, by the one or more computer systems, the identified medical procedure module to the patient;

updating, in a first data storage device, data in a field of a third relational data structure to include first information that specifies whether one or more conditions have been satisfied to initiate an update to a webpage that can be provided by the one or more computer systems to display the second stage section;

responsive to determining, by the one or more computer systems and based on the updated data, that the one or more conditions have been satisfied to initiate an update to the webpage, transmitting, to a device used by the patient over the network, a notification to provide electronic consent, the notification including a link, wherein selection of the link causes rendering, by an application of the device, of a webpage in a display of the device that displays the first stage section of the medical procedure module;

tracking, by the one or more computer systems, a first amount of time the patient reviews the first stage section;

receiving, by the one or more computer systems and from the device used by the patient over the Internet, a fourth relational data structure that includes structured fields that represent second information indicating that the patient has input information that affirms that the patient has reviewed and understood the first stage section;

determining, by the one or more computer systems, whether the first amount of time the patient reviews the first stage section exceeds a predetermined threshold amount of time;

accessing, by the one or more computer systems, program code that correlates the first information, the second information, and data indicating that (i) the determining indicates that the first amount of time exceeds a predetermined threshold or (ii) the determining indicates that the first amount of time does not exceed a predetermined threshold;

when the correlated information includes information specifying that the first amount of time exceeds the predetermined threshold, accessing, by the one or more computer systems, computer code that enhances the first information for use in updating the webpage provided by the one or more computer systems to display the second stage section;

when the correlated information includes information specifying that the first amount of time does not exceed the predetermined threshold:
restricting, by the one or more computer systems, transmittal of the second stage section to the device used by the patient until the information specifying that the patient has input information that affirms that the patient has reviewed and understood the first stage section is received; and
upon receiving the information specifying that the patient has reviewed and understood the first stage section, accessing, by the one or more computer systems, computer code that enhances the first information to initiate an update to the webpage provided by the one or more computer systems to display the second stage section; and electronically obtaining, at least partly based on first information specifying completion of the first stage section and second information specifying completion of the second stage section displayed in the webpage, consent to the medical procedure.

10. The one or more machine-readable hardware storage devices of claim 9, wherein the operations further comprise:
generating, for the first stage section, information and one or more visualizations related to a first stage of the medical procedure;
assigning, to the first stage section, the generated information and the one or more visualizations related to the first stage of the medical procedure;
generating, for the second stage section, information and one or more visualizations related to a second stage of the medical procedure; and
assigning, to the second stage section, the generated information and the one or more visualizations related to the second stage of the medical procedure.

11. The one or more machine-readable hardware storage devices of claim 9, wherein the first stage section comprises information and one or more visualizations related to a first stage of the medical procedure; and
wherein the second stage section comprises information and one or more visualizations related to a second stage of the medical procedure.

12. The one or more machine-readable hardware storage devices of claim 9, wherein medical procedure modules are associated with unique identifiers, and wherein the operations further comprise:
receiving, from a device used by a medical service provider, a message comprising content for a medical procedure module, wherein the message comprises a unique identifier for the content;
searching, in a database storing the medical procedure modules, for a medical procedure module with a unique identifier corresponding to the unique identifier for the content;
identifying, based on searching, a medical procedure module with a unique identifier corresponding to the unique identifier for the content; and
assigning the content to the identified medical procedure module.

13. The one or more machine-readable hardware storage devices of claim 9, wherein the operations further comprise:
receiving a request for a medical procedure module that is related to a medical procedure to be performed on a patient; and selecting, from a set of medical procedure modules, the medical procedure module that is related to the medical procedure to be performed, wherein selecting is based on a type of the medical procedure.

14. The one or more machine-readable hardware storage devices of claim 9,
wherein, after it is determined that the amount of time the patient reviewed the first stage section does not exceed the predetermined threshold amount of time, the method further comprises performing one or more of the following operations:
sending, to the device used by the patient, a message notifying the patient to re-review the first stage section; and
sending, to a device associated with a medical service provider, a notification that that patient may have inadequately reviewed the first stage section.

15. The one or more machine-readable hardware storage devices of claim 9, wherein the medical procedure module comprises a first medical procedure module, wherein the medical procedure comprises a first medical procedure, and wherein the operations further comprise:
retrieving a second medical procedure module for educating the patient about a second medical procedure;
wherein the first medical procedure module differs from the second medical procedure module;
wherein the first medical procedure differs from the second medical procedure.

16. The one or more machine-readable hardware storage devices of claim 9, wherein the operations further comprise:
structuring the first stage section to include a series of trays, wherein a tray includes a collection of information associated with a category specified by the tray.

17. An electronic system comprising:
one or more processing devices; and
one or more machine-readable media configured to store instructions that are executable by the one or more processing devices to perform operations of electronically obtaining consent over a network for performance of a medical procedure, the operations comprising:
tracking, by one or more computer systems, one or more medical appointments by obtaining external data structured using fields of a first relational data structure that is stored in a memory device of an electronic booking system of a medical services provider and used by the external appointment booking system of the medical services provider to represent medical appointments for one or more patients, wherein the external appointment booking system is configured for communication with the one or more computer systems using the Internet that are (i) remote from the memory device of the electronic booking system of the medical services provider and (ii) configured to perform the tracking and automatic assignment of medical procedure modules to patients;
based on the tracking, automatically detecting, by the one or more computer systems, particular data obtained from the structured fields of the relational data structure that is stored in the memory device of the electronic booking system, wherein the particular data (i) represents an upcoming medical appointment for a patient and (ii) includes a key value that is used to identify the patient;
responsive to the detecting, (i) accessing, by the one or more computer systems, a second relational data structure that includes fields that structure data representing an electronic medical record (EMR) associated with the patient using the key value and (ii) analyzing, by the one or more computer systems, the EMR associated with the patient to identify, based on the data structured in the fields of the second relational data structure representing the EMR, one or more items of medical data in the EMR;
generating, by the one or more computer systems, a search query that includes search parameters based on the one or more items of medical data that were identified based on the data structured in the fields of the second relational data structure representing the EMR;
automatically executing, by the one or more computer systems, the generated search query against a database storing a plurality of potential medical procedure modules to identify a medical procedure module associated with one or more criteria that are satisfied by the parameters of the generated search query that include the one or more items of medical data that were identified based on the data structured in the fields of the second relational data structure representing the EMR, wherein the medical procedure module includes sections representing stages of a medical procedure, and wherein the sections include a first stage section and a second stage section, wherein the first and second stages each include sections for obtaining consent for a medical procedure that is represented by the identified medical procedure module;
identifying, based on the automatic execution of the generated search query by the one or more computer systems, a particular medical procedure module that is associated with the one or more criteria that are satisfied by the parameters of the search query that include the one or more items of medical data that were identified based on the data structured in the fields of the second relational data structure representing the EMR;
automatically assigning, by the one or more computer systems, the identified medical procedure module to the patient;
updating, in a first data storage device, data in a field of a third relational data structure to include first information that specifies whether one or more conditions have been satisfied to initiate an update to a webpage that can be provided by the one or more computer systems to display the second stage section;
responsive to determining, by the one or more computer systems and based on the updated data, that the one or more conditions have been satisfied to initiate an update to the webpage, transmitting, to a device used by the patient over the network, a notification to provide electronic consent, the notification including a link, wherein selection of the link causes rendering, by an application of the device, of a webpage in a display of the device that displays the first stage section of the medical procedure module;
tracking, by the one or more computer systems, a first amount of time the patient reviews the first stage section;
receiving, by the one or more computer systems and from the device used by the patient over the Internet, a fourth relational data structure that includes structured fields that represent second information indicating that the patient has input information that affirms that the patient has reviewed and understood the first stage section;

determining, by the one or more computer systems, whether the first amount of time the patient reviews the first stage section exceeds a predetermined threshold amount of time;

accessing, by the one or more computer systems, program code that correlates the first information, the second information, and data indicating that (i) the determining indicates that the first amount of time exceeds a predetermined threshold or (ii) the determining indicates that the first amount of time does not exceed a predetermined threshold;

when the correlated information includes information specifying that the first amount of time exceeds the predetermined threshold, accessing, by the one or more computer systems, computer code that enhances the first information for use in updating the webpage provided by the one or more computer systems to display the second stage section;

when the correlated information includes information specifying that the first amount of time does not exceed the predetermined threshold:
 restricting, by the one or more computer systems, transmittal of the second stage section to the device used by the patient until the information specifying that the patient has input information that affirms that the patient has reviewed and understood the first stage section is received; and
 upon receiving the information specifying that the patient has reviewed and understood the first stage section, accessing, by the one or more computer systems, computer code that enhances the first information to initiate an update to the webpage provided by the one or more computer systems to display the second stage section; and electronically obtaining, at least partly based on first information specifying completion of the first stage section and second information specifying completion of the second stage section displayed in the webpage, consent to the medical procedure.

18. The electronic system of claim 17, wherein the operations further comprise:
 generating, for the first stage section, information and one or more visualizations related to a first stage of the medical procedure;
 assigning, to the first stage section, the generated information and the one or more visualizations related to the first stage of the medical procedure;
 generating, for the second stage section, information and one or more visualizations related to a second stage of the medical procedure; and
 assigning, to the second stage section, the generated information and the one or more visualizations related to the second stage of the medical procedure.

19. The electronic system of claim 17, wherein the first stage section comprises information and one or more visualizations related to a first stage of the medical procedure; and
 wherein the second stage section comprises information and one or more visualizations related to a second stage of the medical procedure.

20. The electronic system of claim 17, wherein medical procedure modules are associated with unique identifiers, and wherein the operations further comprise:
 receiving, from a device used by a medical service provider, a message comprising content for a medical procedure module, wherein the message comprises a unique identifier for the content;
 searching, in a database storing the medical procedure modules, for a medical procedure module with a unique identifier corresponding to the unique identifier for the content;
 identifying, based on searching, a medical procedure module with a unique identifier corresponding to the unique identifier for the content; and
 assigning the content to the identified medical procedure module.

21. The computer-implemented method of claim 3, wherein the medical codes associated with the patient education modules are International Classification of Diseases (ICD) codes.

* * * * *